United States Patent [19]
Fridland et al.

[11] Patent Number: 5,576,177
[45] Date of Patent: Nov. 19, 1996

[54] BIOASSAY FOR REVERSE TRANSCRIPTASE INHIBITORS

[75] Inventors: Arnold Fridland; Brian L. Robbins, both of Memphis, Tenn.

[73] Assignee: St. Jude Children's Research Hospital, Memphis, Tenn.

[21] Appl. No.: 208,109

[22] Filed: Mar. 9, 1994

[51] Int. Cl.$^6$ ............... C12Q 1/70; C12Q 1/68; G01N 33/48

[52] U.S. Cl. ............... 435/5; 435/6; 435/91.51; 435/183; 435/194; 436/63

[58] Field of Search ............... 435/5, 6, 91.51, 435/15, 183, 194; 436/63; 935/36, 77, 82

[56] References Cited

U.S. PATENT DOCUMENTS 5,183,949  2/1993  Kindt et al. ............... 800/2

OTHER PUBLICATIONS

Izuta et al., "The 5'-triphosphates of 3'-azido-3'-deoxythymidine and 2',3'-dideoxynucleosides Inhibit DNA Polymerase γ by Different Mechanisms," *Biochem. and Biophys. Res. Comm.* 179(2):776–783 (1991).

Robbins et al, Antimicrobial Agent & Chemotherapy (Jan. 1994) 38:115–121.

Slusher et al, Antimicrobial Agents & Chemotherapy (Nov. 1992) 36:2473–2477.

Robbins et al, J. Cellular Biochem (Apr. 1993), p. 22, Abstract Q145.

Konig et al, J. Cellular Biochem (1992) p. 36, Abstract Q222.

O'Brien et al, Life Sciences (1993) 52:243–249.

Kuster et al., "A Method for the Quantification of Intracellular Zidovudine Nucleotides," *J. of Infectious Diseases* 164:773–776 (1991).

Lacey et al., "Biochemical Studies on the Reverse Transcriptase and RNase H Activities from Human Immunodeficiency Virus Strains Resistant to 3'-Azido-3'-deoxythymidine," *Biochem. of HIV AZT Resistance* 267(22):15789–15794 (1992).

Lambert et al., "2',3'-Dideoxyinosine (ddI) in Patients with the Acquired Immunodeficiency Syndrome or AIDS-Related Complex," *NEJM* 322(19):1333–1340 (1990).

Ma et al., "New Thymidine Triphosphate Analogue Inhibitors of Human Immunodeficiency Virus–1 Reverse Transcriptase," *J. Med. Chem.* 35:1938–1941 (1992).

Masood et al., "Cellular Pharmacology of the Anti-HIV Agent 2',3'-Didehydro-2',3'-dideoxythymidine" *Proc. of the Amer. Assoc. Cancer Research* 30:594 abstract A2364 (1989).

Meng et al., "AIDS Clinical Trials Group: Phase I/II Study of Combination 2',3'-Dideoxycytidine and Zidovudine in Patients with Acquired Immunodeficiency Syndrome (AIDS) and Advanced AIDS–Related Complex," *The Amer. J. of Medicine* 88 (suppl 5B):27S–30S (1990).

Mitsuya et al., "3'-Azido-3'-deoxythymidine (BW A509U): An Antiviral Agent That Inhibits the Infectivity and Cytopathic Effect of Human T–lymphotropic Virus Type III/lymphadenopathy–associated Virus In Vitro," *Proc. Natl. Acad. Sci. USA* 82:7096–7100 (1985).

Olsen et al., "Interaction of HIV1-RT With Azidothymidine Triphosphate and the Nonnucleoside Inhibitor L–697, 661," *Int. Conf. AIDS* 7(2):A45 abstract PoA 2255 (1992).

(List continued on next page.)

*Primary Examiner*—W. Gary Jones
*Assistant Examiner*—Carla Myers
*Attorney, Agent, or Firm*—Sterne, Kessler, Goldstein & Fox, P.L.L.C.

[57] ABSTRACT

The present invention relates generally to methods and kits for determining the bodily level of a reverse transcriptase inhibitor or, therapeutic compound or metabolite thereof used to treat retrovirus infection, particularly HIV 1 infection.

17 Claims, 4 Drawing Sheets

OTHER PUBLICATIONS

Parker et al., "Inhibition of Human DNA Polymerases and Human Immunodeficiency Virus (HIV) Reverse Transcriptase by a Novel Class of Compounds, Galloylquinic Acids," *Proc. of the Amer. Assoc. for Cancer Res.* 30:578 abstract 2301 (1989).

Parker et al., "Mechanism of Inhibition of Human Immunodeficiency Virus Type 1 Reverse Transcriptase and Human DNA Polymerases $\alpha$, $\beta$, and $\gamma$ by the 5'-Triphosphates of Carbovir, 3'-Azido-3'-deoxythymidine, 2',3'-Dideoxyguanosine, and 3'-Deoxythymidine," *J. Biol. Chem.* 266(3):1754–1762 (1991).

Pei–zhen et al., "An in vitro EIAV RT Model for Screening of Anti–HIV Agents", *Intl. Conf. AIDS* 5:501 abstract B.626 (1989).

Reardon, J. E., "Human Immunodeficiency Virus Reverse Transcriptase; Steady–State and Pre–Steady–State Kinetics of Nucleotide Incorporation," *Biochem.* 31(18):4473–4479 (1992).

Robbins et al., "A Novel Method for the Measurement of Intracellular Zidovudine Triphosphate (ZDV–TP)," *J. Cellular Biochem.* Supp 17E:22 abstract Q145 (1993).

Shirasaka et al., "In Vitro Study of Drug–Sensitivity of HIV Strains Isolated from Patients with AIDS or ARC Before and After Therapy with AZT and/or 2',3'–Dideoxycytidine (ddC)," *Intl. Conf. AIDS* 6(1):185 abstract Th.A.263 (1990).

Skowron, et al., "Alternating and Intermittent Regimens of Zidovudine and Dideoxycytidine in Patients with AIDS or AIDS–Related Complex," *Annals of Int. Medicine* 118(5):321–330 (1993).

Slusher et al., "Intracellular Zidovudine (ZDV) and ZDV Phosphates as Measured by a Validated Combined High–Pressure Liquid Chromatography–Radioimmunoassay Procedure," *Antimicrobial Agents and Chemotherapy* 36(11):2473–2477 (1992).

Tavares et al., "3'-Azido-3'-deoxythymidine in Feline Leukemia Virus–infected Cats: A Model for Therapy and Prophylaxis of AIDS," *Cancer Research* 47:3190–3194 (1987).

Toyoshima et al., "A Sensitive Nonisotopic Method for the Determination of Intracellular Azidothymidine 5'–Mono–, 5'–Di–; and 5'–Triphosphate," *Analytical Biochemistry* 196:302–307 (1991).

Vogt et al., "Experimental Azidothymidine (AZT) Pulse Therapy Leads to Adequate and Prolonged Levels of Intracellular AZT–Triphosphate (AZT–TP)," *Intl. Conf. AIDS* 5:555 abstract M.C.P.83 (1989).

Vrang et al., "Inhibition of the Reverse Transcriptase from HIV by 3'–azido–3'–deoxythymidine Triphosphate and its threo Analogue," *Antiviral Research* 7:139–149 (1987).

Wainberg et al., "Characterization of AZT–Resistant Isolates of HIV–1: Susceptibility to Deoxythiacytidine and Other Nucleosides," *Intl. Conf. AIDS* 6(3):117 abstract S.B.87 (1990).

White et al., "Mechanism of Inhibition by Carbovir Triphosphate of HIV Reverse Transcriptase and Human DNA Polymerases, Compared with the Action of AZT Triphosphate and Dideoxynucleoside Triphosphates," *Intl. Conf. AIDS* 6(1):186 abstract Th.A.266 (1990).

White et al., "A TIBO Derivative, R82913, is a Potent Inhibitor of HIV–1 Reverse Transcriptase with Heteropolymer Templates," *Antiviral Research* 16:257–266 (1991).

Yarchoan et al., "Administration of 3'–Azido–3'–Deoxythymidine, An Inhibitor of HTLV–III/LAV Replication, to Patients with AIDS or AIDS–Related Complex," *Lancet* pp. 575–580 (1986).

Balzarini et al., "Differential Patterns of Intracellular Metabolism of 2',3'–Didehydro–2',3'–dideoxythymidine and 3'–Azido–2',3'–dideoxythymidine, Two Potent Anti–Human Immunodeficiency Virus Compounds," *J. Biol. Chem.* 264(11):6127–6133 (1989).

Boucher et al., "Phase I Evaluation of Zidovudine Administered to Infants Exposed at Birth to the Human Immunodeficiency Virus," *Journal of Pediatrics* 122(1):137–144 (1993).

Butler, W. B., "Preparing Nuclei from Cells in Monolayer Cultures Suitable for Counting and for Following Synchronized Cells through the Cell Cycle," *Analytical Biochemistry* 141:70–73 (1984).

Fischl et al., "The Efficacy of Azidothymidine (AZT) in the Treatment of Patients with AIDS and AIDS–Related Complex," *NEJM* 317(4):185–191 (1987).

Fischl et al., "A Randomized Controlled Trial of a Reduced Daily Dose of Zidovudine in Patients with the Acquired Immunodeficiency Syndrome," *NEJM* 323(15):1009–1014 (1990).

Fletcher et al., "Comparative Pharmacokinetics of Zidovudine in Healthy Volunteers and in Patients With AIDS With and Without Hepatic Disease," *Pharmacotherapy* 12(6):429–434 (1992).

Furman et al., "Phosphorylation of 3'–azido–3'–deoxythymidine and Selective Interaction of the 5'–triphosphate with Human Immunodeficiency Virus Reverse Transcriptase" *Proc. Natl. Acad. Sci. USA* 83:8333–8337 (1986).

Furman et al., "Spectrum of Antiviral Activity and Mechanism of Action of Zidovudine," *The American Journal of Medicine* 85(Supp 2A):176–181 (1988).

Hovanessian et al., "Antiviral Activity of Poly(A).Poly(U) Against HIV in vitro," *Intl. Conf. AIDS* 7(2):113 abstract W.A.1084 (1991).

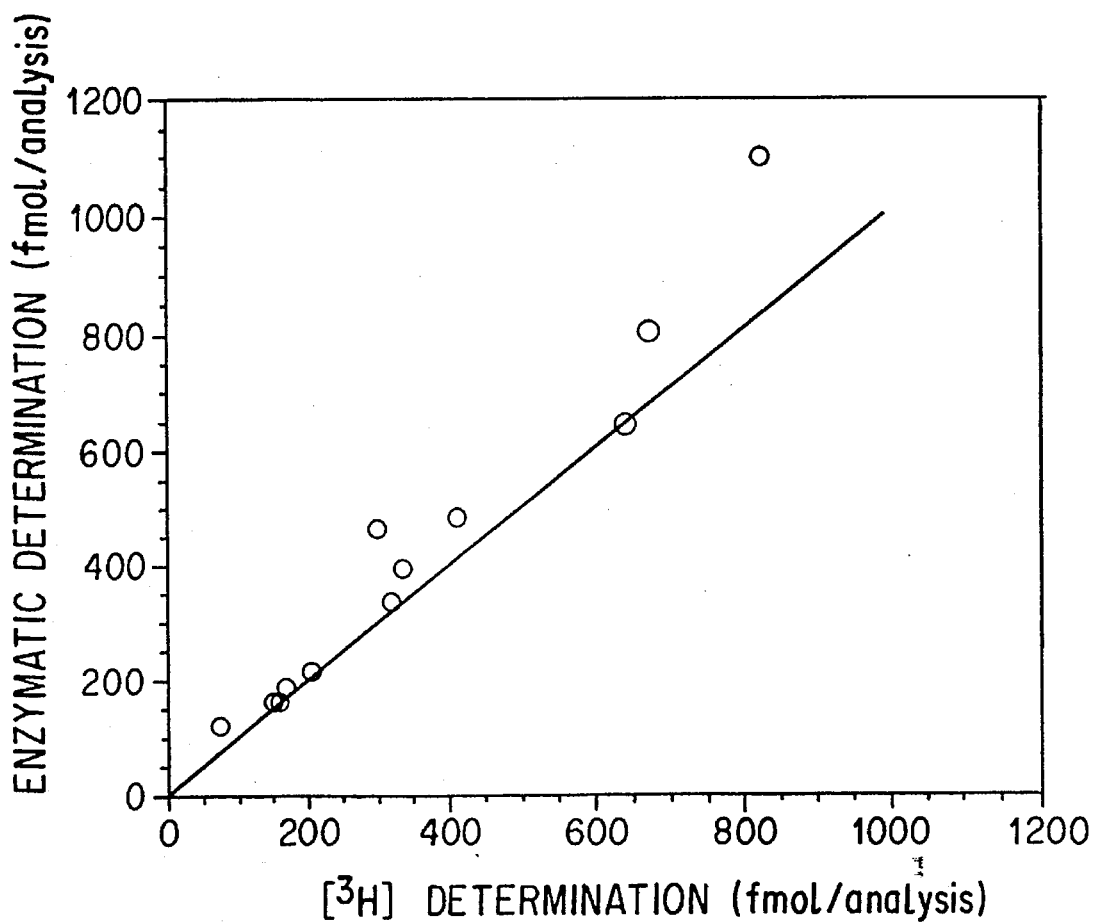
F I G. 3

BIOASSAY FOR REVERSE TRANSCRIPTASE INHIBITORS

This invention was made in part with Government support under PHS grant numbers 1R01 AI27652, 1R01 AI31145, and Cancer Center Support (CORE) grant CA 21765 from the National Institute of Health. The Government has certain rights in the invention.

FIELD OF THE INVENTION

The present invention relates generally to methods for determining reverse transcriptase inhibitor levels in an individual being treated with a reverse transcriptase inhibitor comprising a reverse transcriptase assay.

The invention further relates to methods for determining reverse transcriptase inhibitor levels in an individual being treated with a therapeutic compound used to treat a retrovirus infection comprising a reverse transcriptase assay.

The invention still further relates to kits useful with the assay methods of the invention.

BACKGROUND OF THE INVENTION

Zidovudine (3'-azido-3'-deoxythymidine) is one of three nucleoside analogs approved for the treatment of AIDS and AIDS-related complex (Boucher et al., *J. Pediatr.* 122:137–144 (1993); Fischl et al., *N. Engl. J. Med.* 323:1009–1014 (1990); Fischl et al., *N. Engl. J. Med.* 317:185–190 (1987); Lambert et al., *N. Engl., J. Med.* 322:1333–1340 (1990); Meng et al., *Amer. J. Med.* 88 (Supp. 15B):27S–30S (1990); Skowron et al., *Ann. Inter. Med.* 118:321–330 (1993); Yarchoan et al., *The Lancet* 1:575–580 (1986)).

Investigations of the mode of action of zidovudine have shown that the drug is phosphorylated to its 5'-mono-, di-, and triphosphate derivatives by cellular kinases. Zidovudine-5'-triphosphate is a potent inhibitor of human immunodeficiency virus (herein "HIV") reverse transcriptase and thus of HIV replication (Furman et al., *Proc. Natl. Acad. Sci. USA* 83:8333–8337 (1986); Mitsuya et al., *Proc. Natl. Acad. Sci. USA* 82:7096–7100 (1985)). It is also known that zidovudine triphosphate causes reverse transcriptase chain termination (Izuta et al., *Biochem. Biophys. Res. Comm.* 179 (2):776–783 (1991)).

Much of what is presently known about the intracellular metabolism of zidovudine has been elucidated using radiolabeled drugs in cultured human lymphoid cells. For example, marked differences in the activation and accumulation of zidovudine nucleotides have been noted among different cells upon incubation with zidovudine which correlate with differences in the in vitro effectiveness of the drug (Balzarini et al., *Adv. Exp. Med. Biol.* 253B:407–413 (1990); Balzarini et al., *J. Biol. Chem.* 264:6127–6133 (1989)).

Quantitation of zidovudine metabolites has been performed with in vitro cell systems using radiolabeled zidovudine (Furman et al., *Proc. Natl. Acad. Sci. USA* 83:8333–8337 (1986); Mitsuya et al., *Proc. Natl. Acad. Sci. USA* 82:7096–7100 (1985)). These studies on the mechanism of action of zidovudine have shown that zidovudine is phosphorylated to its mono-, di-, and triphosphate forms via thymidine kinase and other cellular kinases. Zidovudine triphosphate, as the active form of the drug, is directly responsible for inhibition of reverse transcriptase which ultimately results in inhibition of viral replication by zidovudine (Lambert et al., *N. Engl., J. Med.* 322:1333–1340 (1990)). However, determination of zidovudine triphosphate in human clinical studies has proven difficult because the use of radiolabeled zidovudine is not feasible in patients.

Since in vitro results from human cell lines in culture cannot necessarily be extrapolated to the in vivo situation and because differences in drug disposition and clinical effects exist in patients, it is of interest to measure the intracellular level of zidovudine triphosphate, the major active metabolite of the drug. More importantly, the evaluation of the intracellular metabolism and pharmacology of the proximate inhibitor of zidovudine would lead to a better understanding of the pharmacological properties of zidovudine in vivo than can obtained from measurement of plasma pharmacokinetics of zidovudine alone.

Two methods have been described for quantitative determination of intracellular zidovudine metabolites in HIV infected patients. One method involves using a multidimensional high pressure liquid chromatography (herein "HPLC") method but its application to measuring cellular zidovudine nucleotides in patients undergoing therapy has not been evaluated (Toyoshima et al., *Anal. Biochem.* 196:302–307 (1991)). The other method is an indirect assay which utilizes HPLC and radioimmunoassay (herein "RIA"). However, this method is quite cumbersome and requires prior purification of zidovudine metabolites from cell extracts, treatment of extracts with phosphatases and quantitation of the resultant zidovudine with an RIA (Kuster et al., *J. Infect. Dis.* 164:773–776 (1991); Slusher et al., *Antimicrob. Agents Chemother.* 36: 2473–2477 (1992)).

Further, in vitro reverse transcription assays are known whereby the inhibitory effects of zidovudine triphosphate on the polymerization of DNA by reverse transcriptase are detected (Lacey et al., *J. Biochem.* 267 (22): 15789–15794 (1992); Ma et al., *J. Med. Chem.* 35 (11):1938–1941 (1992); Reardon, *J. E., Biochem.* 31 (18):4473–4479 ( 1992); Izuta et al., *Biochem. Biophys. Res. Comm.* 179 (2):776–783 (1991); Parker et al., *J. Biochem.* 266 (3):1754–1762 (1991); Vrang et al., *Antiviral Res.* 7 (3):139–149 (1987); Olsen et al., *Int. Conf. AIDS* 8 (2):PA45 (1992) (Abs. No. PoA 2255); Gronowitz et al., *Int. Conf. AIDS* 7 (2):113 (1991) (Abs. No. WA1086); White et al., *Int. Conf. AIDS* 6 (1):186 (Abs. No. ThA266) (1990); White et al., *Antiviral Res. (Netherlands)* 16/3:257–266 (1991); Furman et al., *Am. J. Med. (USA)* 85/2 A:176–181 (1988); Vogt et al., *Int. Conf. AIDS* 5:555 (1989) (Abs. No. Mcp83)). However, the use of reverse transcriptase assays for measuring bodily levels of zidovudine triphosphate have not been reported.

Herein, we describe a simple and convenient bioassay based on the inhibition of reverse transcriptase activity to measure body levels of reverse transcriptase inhibitors, therapeutic compounds and their metabolites, and particularly to quantify intracellular levels of zidovudine triphosphate in cell extracts. Many bodily tissues and cells may be utilized and analyzed in the methods of the invention. The general reproducibility, simplicity and reliability of the method of the invention have been examined and compared favorably to previously studied procedures.

SUMMARY OF THE INVENTION

The present invention relates generally to methods for determining reverse transcriptase inhibitor levels in an individual being treated with a reverse transcriptase inhibitor comprising a reverse transcriptase assay.

Methods are also provided for determining reverse transcriptase inhibitor levels in an individual being treated with a therapeutic compound or metabolite thereof used to treat a retrovirus infection comprising a reverse transcriptase assay.

Kits are provided for detecting the bodily level of a reverse transcriptase inhibitor comprising: a container means, a substantially purified reverse transcriptase, a nucleic acid primer, a nucleic acid template, and a known concentration of substantially purified zidovudine triphosphate.

BRIEF DESCRIPTION OF THE FIGURES

FIG. 3 depicts a correlation between zidovudine triphosphate levels determined with the reverse transcriptase assay and measured radioisotopically. Peripheral blood mononuclear cells were incubated with labeled zidovudine at final concentrations of 0.5, 5, 10, and 50 µM. These samples were diluted to provide a wide range of zidovudine triphosphate. The concentration of zidovudine triphosphate was determined by both enzymatic and isotopic methods. The results of the two determinations were plotted with the line representing unity.

DETAILED DESCRIPTION OF THE PREFERRED EMBODIMENTS

Figure 1:
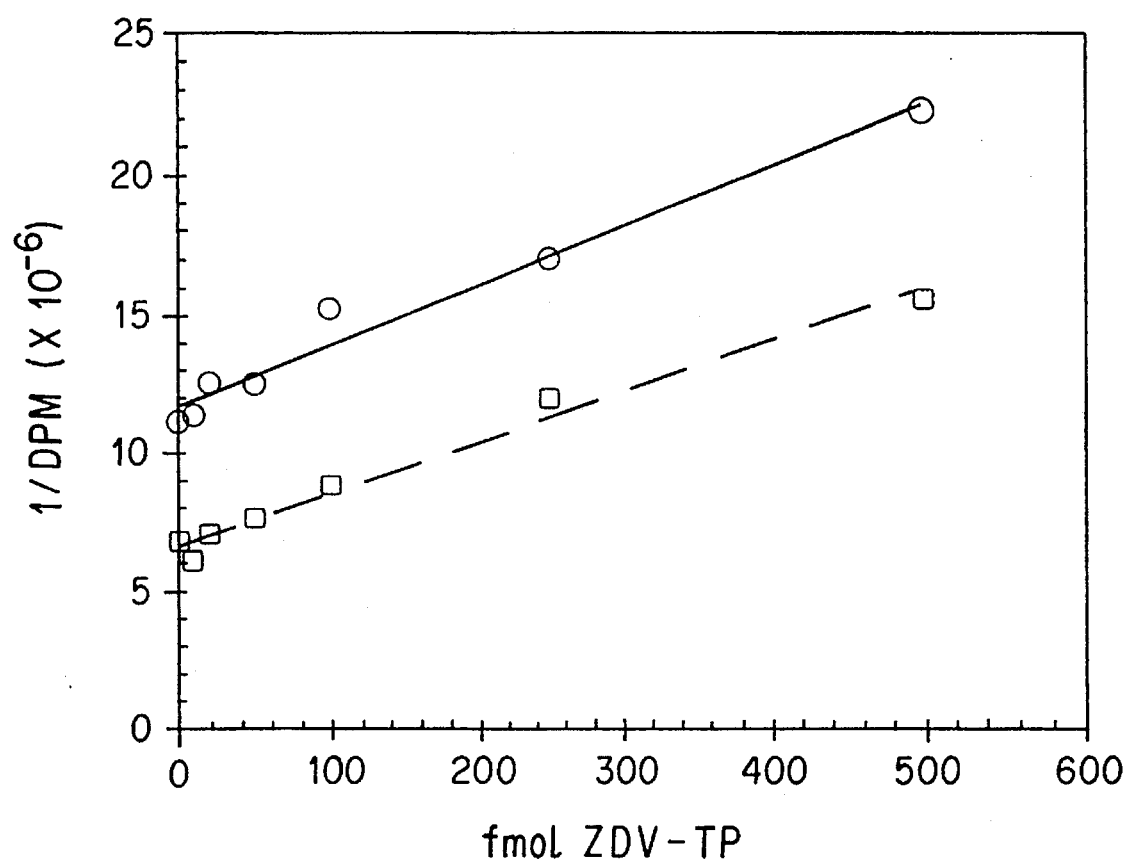
FIG. 1 depicts the effect of zidovudine triphosphate and peripheral blood mononuclear cell extract addition on HIV reverse transcriptase activity. Reverse transcriptase is incubated at 37° C. with 0, 10, 20, 50, 100, 250, and 500 fmol of zidovudine triphosphate in the absence (□) or presence (○) of 4.5 µl of untreated peripheral blood mononuclear cell extract.

This invention relates to the discovery that the bodily level of a reverse transcriptase inhibitor or therapeutic compound can be measured using a simple, sensitive, and reproducible reverse transcriptase bioassay. The present invention is particularly useful for determining reverse transcriptase inhibitor levels in individuals being treated with a reverse transcriptase inhibitor, such as an antiretroviral therapeutic compound, and especially zidovudine, commonly known as AZT. The quantitation of the levels of reverse transcriptase inhibitor will be extremely important to clinicians since it will enable them to ascertain whether the therapeutic regimens being applied to their patients are achieving desired levels of inhibitor in the patient. Therefore, the bioassay of the present invention will provide to the numerous individuals suffering from HIV infection, an important method for determining the efficacy of their therapies.

The discovery of such a simple bioassay has significant utility beyond present bioassays for reverse transcriptase inhibitors such as the RIA or the HPLC assay. The HPLC assay requires expensive equipment that is not conveniently transported to the site of need. By contrast, certain embodiments of the methods of the present invention are simple and inexpensive to perform. Moreover, certain of the kits of the invention will be portable and can be easily transported to the site of need. The RIA requires the use of radionuclides, whereas certain embodiments of the invention do not. Thus, certain of the methods and kits are more safe to use and the waste reagents more simple to dispose of than with the RIA.

A. Bioassay for Determining the In Vivo Level of Reverse Transcriptase Inhibitors and Antiretroviral Therapeutic Agents As used herein the terms "reverse transcriptase assay" and "assay" refer generally to techniques for determining or detecting whether a compound is capable of inhibiting reverse transcriptase, and includes, but is not limited to techniques in which inhibition is demonstrated by a diminution in the reverse polymerization activity of reverse transcriptase.

As used herein, the term "substantially pure" or "substantially purified" is meant to describe a compound which is substantially free of any compound associated with the compound in its natural state. For example, a protein which is substantially free from other proteins, nucleic acids, lipids and carbohydrates is considered to be substantially pure or purified. The term is further meant to describe a compound which is homogenous by one or more criteria of purity or homogeneity used by those of skill in the art. The terms "substantially pure" or "substantially purified" as use herein are not meant to exclude artificial, synthetic, or semi-synthetic mixtures or hybrids.

As used herein, the terms "detecting" and "determining" are used interchangeably and are to be construed as having equivalent meaning.

As used herein, the term "bodily sample" refers generally to a sample from an organism including all cells and fluids of an organism, particularly, but not limited to those cells which are migratory or part of the blood, lymph or cerebrospinal fluid. The term "bodily sample" is to be construed to include but not be limited to blood cells, skin cells, muscle cells, bone cells, cells of the various organs, fluids of the circulatory, lymphatic and central nervous systems as well as inter- and intra-cellular fluids.

As used herein, the term "individual" refers generally to a single specimen or member of an organism-group or species. The term is to be construed to encompass, but not be limited to mammals, birds, reptiles and amphibians, but it is especially directed to humans. The term is also to be construed to include single cells from a species.

The term "metabolite" as used herein refers generally to any form of a compound, particularly a therapeutic compound or reverse transcriptase inhibitor which may be found following the compound being contacted to an individual or organism, and includes forms of a compound comprising an additional chemical structure or moiety, or lacking a chemical structure or moiety present as a part of the compound prior to being contacted to an individual or an organism. The term is to be construed to include, but not be limited to any structure of zidovudine or related compound that exists, is induced, or caused following contacting zidovudine to an individual or an organism, particularly zidovudine triphosphate.

As used herein, the terms "isolated," "isolating," "treated," and "treating" as they relate to a compound or sample, generally refer to preparing a compound to be tested or analyzed in a manner suitable for testing and/or analysis, or preparing an extract containing a compound to be analyzed and/or tested.

As used herein, the term "bodily level" refers generally to the amount or level of a compound in, or derived, isolated or obtained from an individual's body or part of an individual's body. The term is also to be construed to refer generally to the detection or determination of the concentration, amount, mass, or other quantifiable characteristic of a compound or composition of matter in or derived from an individual's body or part of an individual's body.

As used herein the term "reverse transcriptase inhibitor" refers generally to a compound or metabolite thereof that mediates or causes inhibition of a reverse transcriptase enzyme.

Accordingly, the invention provides methods for determining reverse transcriptase inhibitor levels in an individual being treated with a reverse transcriptase inhibitor comprising a reverse transcriptase assay.

The invention also provides methods for determining the bodily level of a reverse transcriptase inhibitor comprising the steps of: obtaining a bodily sample suspected to contain a reverse transcriptase inhibitor; treating the sample to release said reverse transcriptase inhibitor or render the reverse transcriptase inhibitor capable of inhibiting substantially purified reverse transcriptase; contacting the substantially purified reverse transcriptase with the sample treated in the treating step; and detecting the inhibitor in the sample.

It is preferred in the methods for determining reverse transcriptase inhibitor levels or the bodily level of a reverse transcriptase inhibitor that the inhibitor is a metabolite of zidovudine, particularly zidovudine triphosphate.

It is also preferred in the methods for determining or determining the bodily level of a reverse transcriptase inhibitor that the bodily sample comprises a cell, particularly a peripheral blood mononuclear cell or CEM cell.

It is also preferred in the methods for determining reverse transcriptase inhibitor levels that the assay comprises obtaining a cell from said individual.

Bodily samples used in the methods of the invention can be obtained by any of the various techniques known and employed in the art, including, but not being limited to, phlebotomizing, swabbing, tissue aspirating, or lavaging. Skilled artisans will readily recognize the appropriate method for obtaining a bodily sample for any given method of the invention.

As used herein, the term "lowered" refers generally to a quantitative comparison whereby the lowered quantity or level is less than the quantity or level to which it is being compared.

As used herein, the term "untreated" refers generally to an individual that has not been or prior to being contacted with a therapeutic compound or metabolite thereof, or reverse transcriptase inhibitor or metabolite thereof.

It is further preferred in the methods of the invention that the determining or detecting step further comprises the steps of: detecting a level of RNA-dependent DNA polymerization by the reverse transcriptase; and comparing the level of the detecting step with a level of RNA-dependent DNA polymerization detected in a bodily sample from an untreated individual.

It is preferred that the level detected in the treated individual be a lowered level.

Skilled artisans will readily recognize techniques by which levels of RNA-dependent DNA polymerization can be detected, determined or quantitated such as, for example, by measurement of incorporation of labeled nucleotides in the nucleic acid polymerized, measuring the number of certain residues in the nucleic acid polymerized or spectrographically measuring the absorptivity of the nucleic acid polymerized. Skilled artisans will also recognize numerous hybridization techniques whereby the polymerization can be detected, determined or quantitated, such as, for example, by chromatographic separation of polymerized products followed by hybridization with a labeled nucleic acid (See, for example, Haymes, et al. (in: Nucleic Acid Hybridization, A Practical Approach) IRL Press, Washington, DC (1985)). Another technique that may be employed to determine the level of polymerization is by labelling the template ribonucleic acid and detecting a shift in the level of incorporated label to unincorporated label over time. This technique relies on the RNase activity of reverse transcriptase (See, generally, Stryer, L. *Biochemistry*, 2nd Edition, W. H. Freeman and Co., San Francisco, Calif. (1981) for a general discussion of the mechanism of reverse transcriptase activity).

It will be understood by skilled artisans that the detection step or steps of the invention can be enhanced by labeling the detection means. For example, detection of polymers synthesized by reverse transcriptase (herein "polymerization products") can be enhanced by labeling nucleotide monomers that will be incorporated into the polymerization products. One skilled in the art will immediately recognize that labeling materials will also be useful to label the polymerization products following their synthesis. Skilled artisans will know which compounds are useful for the detection of polymerization products, such as, for example, hybridization probes. Label will also be useful to enhance the detection of an antibody used in the methods of the invention. Labels useful in the methods of the present invention include, but are not limited to, flourescers, ligands, chromophores, chromogens, luminescers, including chemoluminescers and bioluminescers, and radionuclides. Skilled artisans will be able to select an appropriate label for any given means of detection, such means including for example, nucleotide monomers, oligonucleotides, antibodies, lectins, streptavidin-biotin, oligonucleotide intercalating agents and peptides, such as those useful for nucleic acid binding. Skilled artisans will be able to use such means of detection using techniques known in the art. See, for example, Sambrook (Sambrook et al., *Molecular Cloning—A Laboratory Manual* (2d ed.), Cold Spring Harbor Labs, Cold Spring Harbor, N.Y. (1989)).

As used herein, the term "template" refers generally to a nucleic acid molecule which a reverse transcriptase enzyme is capable of using for a reverse transcription reaction to mediate polymerization of DNA. The template molecule may be reverse transcribed either partially or fully, having either substantially all of its nucleotide residues reverse transcribed or any number of its residues reverse transcribed. It is preferred that the nucleic acid template be comprised of the ribonucleic acid, however, certain ribonucleic derivatives will be useful as a template.

The term "primer" refers generally to a nucleic acid molecule capable of hybridizing to the template nucleic acid and priming reverse transcription on the template. The term is to be construed to encompass, but not be limited to, deoxyribonucleic acid and derivatives thereof.

It is further preferred in the methods of the invention that the detecting or determining step further comprises contacting substantially purified reverse transcriptase with a template and primer.

Skilled artisans will understand which templates and primers will be useful in the methods of the invention. Templates and primers useful for reverse transcription are well known in the art and many are commercially available. Any template and primer that will facilitate polymerization of a DNA molecule by reverse transcriptase will be useful in the methods of the invention. Skilled artisans will be easily able to determine which templates and primers are useful in the invention by providing a template and primer to be tested in the presence of reverse transcriptase, appropriate buffers, and nucleotides to detect polymerization of DNA by reverse transcriptase (refer to Examples 1 and 6 for examples of reagents useful for reverse transcription).

The primer and template may be separately introduced into the methods of the invention or may be hybridized prior to use in the methods of the invention. Primers that are hybridized prior to use in the methods of the invention are referred to generally as "primer-template" and may be hybridized using any of the methods of nucleic acid hybridization known in the art. See, for example, Haymes, et al. (in: Nucleic Acid Hybridization, A Practical Approach) IRL Press, Washington, D.C. (1985); and Sambrook et al., *Molecular Cloning—A Laboratory Manual* (2d ed.), Cold Spring Harbor Labs, Cold Spring Harbor, N.Y. (1989)).

It is preferred in the methods of the invention that the template and primer (primer-template) be poly[rA]-oligo [dT]$_{12-18}$. This preferred primer-template is commercially available.

The methods of the invention will be useful in designing and tailoring therapeutic regimens for compounds capable of inhibiting reverse transcriptase to be used as therapeutic compounds for viral infection. Such compounds have broad application in the treatment of retrovirus infection, particularly HIV infection and AIDS. The methods will also likely be useful for individuals infected by a hepadnavirus, especially Hepatitis B virus. Moreover, individuals undergoing treatment with a reverse transcriptase inhibitor can be monitored using the bioassay of the present invention. The skilled artisan administering such therapy will be able to use the bioassay to determine the bodily level of a reverse transcriptase inhibitor in the individual being treated and determine if the level is appropriate to achieve the desired therapeutic goals. If the skilled artisan determines that the levels are too high, the dosage of the therapeutic compound can be lowered. If the level of the compound is too low, the dosage can be increased. The methods of the invention are particularly useful for quantitating the level of HIV and AIDS therapeutic agents, especially zidovudine and metabolites thereof. See, Physicians' Desk Reference, 48th Edition, Medical Economics Data Production Co., Montvale, N.J., 1994 for therapeutic doses of certain reverse transcriptase inhibitory compounds used in human therapy.

Accordingly, it is preferred in the methods for determining the bodily level of a reverse transcriptase inhibitor that the sample is from an individual suspected of having a disease selected from the group consisting of: HIV 1 or HIV 2 infection, AIDS, Kaposi's sarcoma, pneumocytis pneumonia, mycobacterium infection, AIDS Related Complex, AIDS dementia or systemic candidiasis.

The invention also provides methods for determining reverse transcriptase inhibitor levels in an individual being treated with a therapeutic compound used to treat a retrovirus infection comprising a reverse transcriptase assay.

Methods are also provided for determining the bodily level of a therapeutic compound or a metabolite thereof used to treat retrovirus infection comprising the steps of: obtaining a bodily sample from an individual receiving a therapeutic compound and suspected to contain the compound or a metabolite of the compound; treating the sample to release said reverse transcriptase inhibitor to release said reverse transcriptase inhibitor or render the compound or the metabolite capable of inhibiting substantially purified reverse transcriptase; contacting the substantially purified reverse transcriptase with the sample treated as in the treating step; and detecting the compound or the metabolite in the sample.

While the discovery of a convenient assay to determine the reverse transcriptase inhibitor levels in an individual is particularly useful to determine levels of zidovudine and zidovudine triphosphate, therapeutic compounds and reverse transcriptase inhibitors and metabolites thereof useful in any of the methods of the invention also include, but are not limited to dideoxynucleotide triphosphate analogs, including 2',3'-dideoxynucleoside 5'-triphosphates (Izuta, S. et al., *Biochem. Biophys.* 179 (2):776–783 (1991)); including, for example, dideoxyinosine and dideoxycytidine (Shirasaka, T. et al., *Int. Conf. AIDS* 6(1), Abs. No. Th.A.23, p. 185 (1990); anti-reverse transcriptase antibodies and sFvs; Carbovir (carbocyclic analog of 2',3'-didehydro-2',3'-dideoxyguanosine), (White, E. L. et al., *Int. Conf. AIDS* 6 (1), Abs. No. Th.A.266, p. 186 (1990)); 3'-azido-3'-deoxythymidine 5'-[α,β-imido]-triphosphate, (Furman, P. A., et al., *Proc. Natl. Acad. Sci. USA* 83:83333–83337 (1986)); 3'-azido-3'-deoxythymidine 5'-[α,β-imido triphosphate (Tavares, L. et al., *Cancer Res.* 47:3190–3194 (1987)); dideoxythymidine 5'-[α,β-imido]-triphosphate (Ma, Q.-F. et al., *J. Med. Chem.* 35:1938–1942 (1992)); 3'-azidothymidine 5'-[β,γ-imido]-triphosphate (Ma, Q.-F. et al., *J. Med. Chem.* 35:1938–1942 (1992)); 5'-[α,β:β,γ-diimido]-triphosphate 3'-deoxy-2',3'-didehydrothymidine 5'-triphosphate (Ma, Q.-F. et al., *J. Med. Chem.* 35:1938–1942 (1992)); R82913 ((+)-S-4, 5, 6, 7-tetrahydro-9-2 chloro-5-methyl-6-(3-methyl-2-butenyl)-imidazo[4,5,1 -jk][1,4]-benzodiazepin(1H)-thione (a TIBO derivative)), (White, E. L. et al., *Antiviral Res. (Netherlands)* 16/3:257–266(1991 ) ); 3'-deoxy- 2',3'-didehydro-5' triphosphate (Reardon, J. E., *Biochem.* 31 (18):4473–4479 (1992)); 2',3'-dideoxythymidine triphosphate; 5'-triphosphates of 3'-azido-3'-deoxythymidine and 2', 3'-dideoxynucleosides (Reardon, J. E., *Biochem.* 31 (18):4473–4479 (1992)); 5'-triphosphates of carbovir (Parker, W. B. et al., *J. Biol. Chem.* 266 (3):1754–1762 (1991)); 3'-deoxythimidine, and threo- and erythro- isomers of 3'-azido- 3'-deoxythimidine triphosphate (Vrang, L. et al., *Antiviral Res.* 7: 139–149 (1987)); 2',3'-didehydro-2',3'-dideoxythimidine (D4T) (Wainberg, W. A. et al., *Int. Conf. AIDS* 6 (3), Abs. No. S.B.87, p. 117(1990)); purines comprising a 2',3'-dideoxyribose moiety (Masood, R. et al., *Proc. Ann. Meet Am. Assoc. Cancer Res.* 30:A2364 (1989)); nucleosides comprising a 2',3'-didehydro-2',3'-deoxyribose moiety (Masood, R. et al., *Proc. Ann. Meet Am. Assoc. Cancer Res.* 30:A2364 (1989)); 2',3'-dideoxythymidinene (ddE Thd) (Masood, R. et al., *Proc. Ann. Meet Am. Assoc. Cancer Res.* 30:A2364 (1989)); galolyl derivatives of quinic acid, particularly 3' 4' 5-tri-O-galoylquinic acid (Tri GQA), and 3, 4-di-O-galloyl-5-digalloylquinic acid (Tetra GQA) (Parker, W. B. et al., *Proc. Annu. Meet. Am. Assoc. Cancer Res.* 30:A2301 (1989)); Tetra GQA plus 3'-azido-3-deoxy thymidine triphosphate or phosphonoformic acid (Parker, W. B. et al., *Proc. Annu. Meet. Am. Assoc. Cancer Res.* 30:A2301 (1989)); Merck compound L-697,661 (Olsen, D. B. et al., *Track A: Poster Basic Science, Abs. PoA* 2255, p. 45 (1992); 3'-azido-2',3'-dideoxyadenosine AZA (Shirasaka, T. et al., *Int. Conf. AIDS* 6 (1), Abst. No. Th.A.263, p. 185 (1990); 3'-azido-2'-3'-dideoxyguanosine (AZG), carbovir triphosphate, including 5 '-triphosphates of carbovir (White, E. L. et al., *Antiviral Res. (Netherlands)* 16/3:257–266 (1991)); carbovir monophosphate; (-Et, -nPr, -nPre, -iPre, -Ce) 5'-triphosphates of 5'-substituted 2'-deoxyuridine; phosphonoacidic acid (Pei-Zhen, *Int. Conf. AIDS* 5, Abs. #B.626, p. 501 (1989)); phosphonoformic acid (Pei- Zhen, *Int. Conf. AIDS* 5, Abs. #B.626, p. 501 (1989)); zidovudine monophosphate (Lacey, S. F. et al., *Biochem. HIV AZT Resist.*:15789–15794 (1992)); zidovudine diphosphate; 2', 3'-dideoxynucleosides; R 12913; Ribavirin poly(A)•poly(U), (Hovanessian, A. et al., *Int. Conf. AIDS* 7 (2):113, Abs. No. W.A.1084 (1991)); AZT plus interferon; anhydro-AZT; deoxy-thiacytidine (Wainberg, M. A. et al., *Int. Conf. AIDS* 6 (3), Abs. No. S.B.87, p. 117 (1990)); and anhydro-N3, -UdR. It is preferred in the methods for determining reverse transcriptase inhibitor levels or the bodily level of a reverse transcriptase inhibitor or therapeutic agent or metabolite thereof that the compound or metabolite be selected from the group consisting of these compounds above.

It is more preferred in the methods for determining reverse transcriptase inhibitor levels or the bodily level of a therapeutic compound or metabolites thereof, that the metabolite inhibitor is a metabolite of zidovudine.

It is most preferred in the methods for determining reverse transcriptase inhibitor levels or the bodily level of a therapeutic compound or a metabolite thereof, that the metabolite inhibitor is zidovudine triphosphate.

It is also preferred in the methods for determining reverse transcriptase inhibitor levels or the bodily level of a therapeutic compound or metabolite thereof, that the bodily sample comprises a cell, particularly a peripheral blood mononuclear cell.

Cells of the invention can be isolated in any of the many ways known in the art for isolating cells. Skilled artisans will recognize that cells may be obtained from an individual and used directly or maintained in culture prior to being used in the methods of the invention. Cells that are maintained in culture prior to being used in the methods of the invention may be maintained, for example, in standard tissue culture medium. It is preferred that cells be maintained in RPMI-1640 supplemented with 10% newborn calf serum, and be stimulated prior to use by the addition of phytohemagglutinin-P (herein "PHA-P") and IL-2. Skilled artisans will recognize and be able to use other techniques known in the art that are useful for stimulating the cells prior to their use in the methods of the invention.

Cell numbers may be determined by techniques known in the art, such as, for example, enumeration by coulter counter or by using a microscope and reticle (hemocytometer). See, for example, Butler, W. B., *Analytical Biochem.* 141:70–73 (1984).

Bodily samples of the invention such as cells may be isolated and treated prior to use in the methods of the invention by, for example, the preparation of cell extracts. Skilled artisans will recognize many methods for preparing cell extracts. It is preferred that cells are isolated from individuals, centrifuged, resuspended in culture media, layered onto and spun through oil, removed and extracted with methanol and buffer on ice. It is also preferred that following the removal of debris by centrifugation, extracts are stored by freezing until used. Alternatively, it is preferred that cells from individuals are suspended in media and pelleted by centrifugation, extracted with cold methanol, after which the cell debris is removed by centrifugation and the supernatant (cell extract) is stored by freezing. It is further preferred that immediately prior to use, the extracts are dried and resuspended in a buffer useful in the reverse transcriptase bioassay.

The invention provides preferred methods for determining reverse transcriptase inhibitor levels or the bodily level of a therapeutic compound or metabolite thereof in which the detecting step further comprises the steps of: detecting a level of RNA-dependent DNA polymerization by the reverse transcriptase; and comparing the level of the detecting step with a level of RNA-dependent DNA polymerization detected in a bodily sample from an untreated individual.

Detection of levels of polymerization can be carried out as explained elsewhere herein.

It is further preferred in the methods for determining reverse transcriptase inhibitor levels or the bodily level of a therapeutic compound or metabolite thereof, that the detecting step further comprises contacting substantially purified reverse transcriptase with a template and primer.

Reverse transcriptase reactions whereby DNA is polymerized via reverse transcription can be carried out in many ways. Skilled artisans will recognize the appropriate buffers and pH ranges useful for reverse transcriptase function and reverse transcription of nucleic acids. It is preferred in the methods of the invention that the reactions be carried out in small volumes of reagents, such as between about 1 and 50 µl, particularly between about 5 and 20 µl, and especially in about 10 µl. In these preferred embodiments, small volumes of sample are mixed with equal volumes of reaction mixture to provide a final concentration of between about 0.1 and 1 µCi of TTP. It is preferred that the concentration of TTP be about 0.5 µCi. It is most preferred that the reaction mixture has a final concentration of about 50 mM Tris (pH 8.5), about 6 mM Mg $Cl_2$, about 10 mM dithiothreitol (DTT), about 2.0 mgs bovine serum albumin (BSA), about 0.5 µCi TTP, about 80% mM KCl, and about 0.05% Triton X-100.

In the methods of the invention it is preferred that the reverse transcriptase reaction be initiated by the addition of between about 0.2 and 2 µl of substantially purified reverse transcriptase (containing about 1 ng of protein). It is more preferred that the reaction be initiated by the addition of between about 0.5 and 1.5 µl of substantially purified reverse transcriptase. It is most preferred that the reaction be initiated by about 1.0 µl of substantially purified reverse transcriptase.

Incubation of the reverse transcriptase reaction reagents should be allowed to proceed for a time sufficient for the reaction to produce polymerization products at the temperature used for the reaction. It is preferred that the reaction proceed from between about 20 and 80 minutes at about 37° C. It is more preferred that the reaction be allowed to proceed for between about 30 and 70 minutes at about 37° C., and it is most preferred that the reaction be allowed to proceed for about 1 hour at about 37° C. Skilled artisans will easily be able to determine the appropriate temperature range for efficient or useful reverse transcriptase activity to occur. While this temperature range will vary for different reverse transcriptases, skilled artisans will be able to determine a useful range, such as, for example, by plotting enzyme activity against temperature. See, generally Walsh, C., *Enzymatic Reaction Mechanisms*, W. H. Freeman & Co., San Francisco, Calif. (1979); Stryer, L. *Biochemistry*, 2nd Edition, W. H. Freeman and Co., San Francisco, Calif. (1981).

Skilled artisans will be able to modify the reaction mixture and reagents to achieve useful reverse transcriptase activity using methods known in the art. Moreover, any reverse transcriptase enzyme reaction mixture known in the art may be used in the methods of the invention. See, for example, U.S. Pat. No. 5,183,949 in which a reaction mixture is disclosed in FIG. 1.

Following incubation, the reaction may be stopped by the addition of a compound that will allow for substantially no continued polymerization by reverse transcriptase or by a physical treatment that will render the reverse transcriptase substantially non-functional, such as heating or freezing. It is preferred that reverse transcription be substantially stopped by ethylenediamine tetraacetate (EDTA) and/or sodium dodecyl sulfate (SDS).

The methods of the invention are generally applicable to the detection of inhibitors of any reverse transcriptase. Skilled artisans will be able to derive reverse transcriptase from many sources using techniques known in the art. For example, substantially purified reverse transcriptase of the invention can be derived from any virus or cell comprising a reverse transcriptase gene or expressing reverse transcriptase, such as, by cloning and expressing a reverse transcriptase gene or extracting or isolating reverse transcriptase protein from virally infected cells. Reverse transcriptase can also be purchased commercially.

Reverse transcriptases of the invention include variants or routants of any reverse transcriptase that exhibit polymerization activity or can mediate reverse transcription. Skilled artisans can easily ascertain whether a variant or mutant of reverse transcriptase has polymerase or reverse transcription activity by performing a simple polymerization or reverse transcription assay using techniques known in the art or as described elsewhere herein.

Reverse transcriptases useful in the methods of the invention include, but are not limited to those derived from retroviruses, such as of the genus Cisternavirus A; Oncovirus B, including mouse mammary tumor viruses (MMTV-S (Bitmer's virus), MMTV-P (GR virus), MMTV-L); Oncovirus C, such as Rous sarcoma virus, Rous-associated virus, chicken sarcoma viruses, leukosis viruses, reticuloendotheliosis viruses, pheasant viruses, murine sarcoma viruses, murine leukosis virus G (Gross or AKR virus), murine leukosis viruses (MLV-F, MLV-M, MLV-R (Friend, Maloney, Rauscher viruses)), murine radiation leukemia virus, murine endogenous viruses, rat leukosis virus, feline leukosis viruses, feline sarcoma virus, feline endogenous virus (RD114), hamster leukosis virus (HLV), porcine leukosis virus, bovine leukosis virus, primate sarcoma viruses (woolly monkey, gibbon, ape), primate sarcoma-associated virus, primate endogenous viruses (baboon endogenous virus, stumptail monkey virus, MAC-1, owl monkey virus (OMC-1)); Oncovirus D, including reptilian viruses, such as the viper virus, and non-reptilian viruses such as Mason-Pfizer monkey virus (MPMV), langur virus, and squirrel monkey virus; Lentivirus E, including Visna virus of sheep and Maedi virus; and Spumavirus F, including foamy viruses of primates, cats, humans, and bovids.

Reverse transcriptase of the invention can also be derived from any of the human retroviruses, particularly the human T cell leukemia viruses and human immunodeficiency viruses, as well as from the hepadnairuses, including hepatitis viruses A, B, C, non-A/non-B and delta agent.

Reverse transcriptases useful in the invention includes ones derived from: Caulimoviruses, avian myoblastosis virus, simian immunodeficiency viruses, feline immunodeficiency viruses, and equine infectious anemia viruses.

It is preferred that reverse transcriptase of the invention be derived from a retrovirus.

It is more preferred that reverse transcriptase of the invention be derived from a human retrovirus, particularly human T cell leukemia viruses and human immunodeficiency viruses.

It is most preferred that reverse transcriptase of the invention be derived from human immunodeficiency virus 1 (HIV 1).

Accordingly, it is preferred in the methods for determining reverse transcriptor inhibitor levels or the bodily level of a reverse transcriptase inhibitor or a therapeutic compound or metabolite thereof, that the substantially purified reverse transcriptase is selected from the group consisting of: Cisternavirus A, Oncovirus B, Oncovirus C, Oncovirus D, Hepadnavirus, Caulimoviruses, simian immunodeficiency viruses, equine infectious anemia virus, human T cell leukemia virus, and human immunodeficiency virus.

Skilled artisans will be able to use the methods of the invention for assaying individuals of many species and in many settings. For example, the assay can be adapted for use to test an individual of any species afflicted by retrovirus infection or infection caused by a virus having reverse transcriptase activity. Skilled artisans will recognize that the various embodiments of the invention will be useful in human and veterinary clinical settings, such as laboratories and hospitals.

Reverse transcriptase inhibition caused by a therapeutic compound or reverse transcriptase inhibitor can be determined, for example, by comparison to inhibition of reverse transcriptase by known amounts of reverse transcriptase inhibitor or therapeutic compound from untreated cells, both in buffer and in the presence of cell extracts. Standard curves may be generated by methods known in the art based on these enzyme activity comparisons, in order to determine the inhibition of the reverse transcriptase and estimate the amount of therapeutic compound or reverse transcriptase inhibitor in an assay sample. Inhibition of reverse transcriptase can be determined in many ways known and used by skilled artisans, such as for example, by measuring nucleotide incorporation in comparison to controls. Inhibition can also be determined in a competitive inhibition assay wherein samples suspected to contain inhibitor are added both to reaction mixes comprising and not comprising a different reverse transcriptase inhibitor. Standard techniques can be used to evaluate competitive inhibition and these values can be compared to values for samples from untreated individuals. See, for example, Stryer, L. *Biochemistry*, 2nd Edition, W. H. Freeman and Co., San Francisco, Calif. (1981) for a general discussion of enzyme kinetics and inhibition; Remington's Pharmaceutical Sciences, 18 Edition, Mack Publishing Co., Easton, Pa. (1990) for a general discussion of displaying graphical data.

The methods of the invention will be useful to detect bodily levels of reverse transcriptase inhibitor or therapeutic compound or metabolite in individuals of a broad range of species. This is particularly due to the broad range of reverse transcriptases useful in the assay. Skilled artisans will be able to determine which reverse transcriptases to use in a given species or disease using techniques known in the art. For example, determining which reverse transcriptase to use can depend on a diagnosis of the disease in an individual of the species. For instance, a diagnosis of HIV infection or AIDS would indicate to the skilled artisan to use HIV reverse transcriptase in the methods of the invention.

B. Bioassay Kits for Determining the In Vivo Level of a Reverse Transcriptase Inhibitor The simplicity and clinical utility of the methods of the invention can be facilitated by the production of convenient kits comprising reagents useful in the methods of the invention. Kits will be especially useful for clinics and hospitals that treat numerous patients infected with retrovirus, including HIV-1 and 2, patients with AIDS, and patients infected by hepatitis virus.

Kits will also greatly facilitate the determination of appropriate dosage regimens by skilled artisans since they will enable a skilled artisan to determine the bodily levels of therapeutic compounds and reverse transcriptase inhibitors used in the treatment of retrovirus infection.

Certain of the embodiments of the invention provide for a hand-held, enclosed bioassay device that can be conveniently discarded after use. These enclosed kits will allow clinicians to safely use and dispose of biohazard-contaminated reagents.

Accordingly, the invention provides kits for detecting the bodily level of a reverse transcriptase inhibitor comprising a container means substantially purified reverse transcriptase, a nucleic acid primer, a nucleic acid template, and a known concentration of substantially purified therapeutic agent, therapeutic agent metabolite, or reverse transcriptase inhibitor, particularly zidovudine triphosphate.

Certain of the kits of the invention will comprise a container means further comprising a panel of samples of therapeutic compound or reverse transcriptase inhibitor of known concentrations. These samples will allow skilled artisans to carry out reactions using the methods of the invention in order to create a standard curve to facilitate the determination of bodily levels of a therapeutic compound or reverse transcriptase inhibitor.

It is preferred that the kits of the invention be hand-held, constructed of durable materials and comprising a transparent reaction vessel means so that reaction results can be readily determined by viewing the kit device.

It is more preferred that the kit device comprises a reaction vessel means useful to perform a reaction in, and wherein the reaction comprises a bodily sample, reagents and substantially purified reverse transcriptase capable of polymerizing DNA by reverse transcription.

It is most preferred that the reaction vessel means be enclosed so that once the reaction has begun, substantially none of the compounds in the reaction vessel means can escape from the container means of the kit device.

It is further preferred that the kits of the invention further comprise labelled dATP, dTTP, dGTP or dCTP.

EXAMPLES

Materials and Methods

The following materials and methods were used in the Examples provided below.

Reagents. [$^3$H]-zidovudine (~20 µCi/mmol), [$^3$H]-thymidine triphosphate (TTP), and zidovudine triphosphate were purchased from Moravek Biochemical, Brea, Calif. Recombinant HIV reverse transcriptase was purchased from American Biotechnologies Inc., Cambridge, Mass. Zidovudine and zidovudine-monophosphate were a gift from Dr. David Johns at the National Cancer Institute, Washington, D.C. Human recombinant IL-2 was obtained from Boehringer Mannheim, Indianapolis, Ind. and Lymphocyte Separation Media (LSM, Ficoll-Hypaque) was purchased from the Oregon Teknika Corp., Durham, N.C. The Sephadex G-50 fine, poly[rA], and oligo[dT]$_{12-18}$ were obtained from Pharmacia LKB Biotechnology Piscataway, N.J. The RIA kits for zidovudine analysis were purchased from INCSTAR, Stillwater, Minn. PHA-P was purchased from Sigma Chemical Co., St. Louis, Mo. Other chemicals were purchased from Sigma Chemical Co., St. Louis, Mo., Fisher Scientific in Fair Lawn, N.J., or Calbiochem in La Jolla, Calif. Tissue culture media RPMI-1640, Hank's balanced salt solution (HBSS), glutamine, and fetal calf serum were purchased from BioWhittaker, Baltimore, Md.

Cells. CCRF/CEM cells were obtained from American Type Culture Collection (Rockville, MD) and maintained in RPMI-1640 medium supplemented with 10% heat-inactivated newborn calf serum. Peripheral blood mononuclear cells (peripheral blood mononuclear cell) were isolated as described below.

Peripheral blood mononuclear cell isolation. Heparinized blood from normal human volunteers or asymptomatic HIV seropositive individuals was diluted 1:1 with HBSS, layered onto LSM (Ficoll hypaque) and then separated by centrifugation for 30 min at 400×g. The mononuclear cell layer was removed, washed once with growth media, counted, and pelleted by centrifugation. The cells were then resuspended in growth medium (RPMI containing 10% fetal calf serum) and the residual erythrocytes lysed by the addition of 3 volumes of cold water for 30 seconds. Erythrocyte lysis was stopped by the addition of 1 volume of 0.6M sodium chloride, and the mononuclear cells were pelleted by centrifugation.

Culture of human peripheral blood mononuclear cells. The peripheral blood mononuclear cells were suspended in growth media and transferred to plastic tissue culture flasks. The monocyte/macrophage cells were allowed to adhere to the flask for at least 60 min after which the non-adherent cells comprises primarily of lymphocytes were transferred to a new flask. The cells were stimulated by addition of 5 µg/ml of PHA-P and 10 units/ml of IL-2 and incubated for 72 hours at 37° C. prior to use. Fresh media was added every 24 hours to maintain the IL-2 concentration. If quiescent cells were required the PHA-P and IL-2 were omitted and the cells were used the following day.

Enumeration of cell numbers. All cell numbers were determined with a coulter counter. When cell clumping prevented normal determination of cell numbers, especially in stimulated peripheral blood mononuclear cell cultures, cell counting was accomplished by counting nucleic (Butler, W. B., Anal. Biochem. 141:70–73 (1984)).

Preparation of cell extracts. Extracts suitable for the analysis of intracellular zidovudine metabolites were prepared either from cells (CEM and quiescent or activated peripheral blood mononuclear cells) incubated with unlabeled of [$^3$H]zidovudine, as well as from fresh peripheral blood mononuclear cells from zidovudine-treated HIV seropositive individuals. Cultured cells incubated with [$^3$H] zidovudine were first harvested by centrifugation at 1000×g for 5 min. The cell pellets were resuspended in 1 ml of residual media and layered onto 150 µl of nyosil oil, and spun through the oil. The media above the oil layer was removed, and any residual media was removed by rinsing the area above the oil layer by two gentle water washes. Finally, the oil was removed and the cells were extracted with 70% methanol+15 mM Tris-HCl buffer (pH 7.4) for at least 15 min on ice. The debris was removed by centrifugation and the samples stored at −20° C. until required.

Uncultured peripheral blood mononuclear cells from zidovudine-treated patients were resuspended in 1 ml of media and transferred to a 1.5 ml centrifuge tube, spun 1 min at 14,000 rpm, the media removed, and pulsed again to allow removal of any residual media. The cells were extracted for at least 15 min with 200 µl of ice cold 70% methanol per 1×10$^7$ cells. The cell debris was removed by centrifugation for 15 min at 14,000 rpm and the supernate stored in −20° C. until required for analysis. Prior to use, the extracts were dried under vacuum and resuspended in 50 µl of 5 mM Tris-HCl buffer (pH 8.5); extracts from 0.5×10$^7$ CEM cells or 1×10$^7$ cultured peripheral blood mononuclear cells were reconstituted in 200 µl buffer.

Example 1

Reverse Transcriptase Assay

Reverse transcriptase assays were performed using substantially purified HIV-1 reverse transcriptase and poly[rA]

-oligo[dT]$_{12-18}$ as primer-template. The reactions were carried out in a total volume of 10 µl; a 4.5 µl volume of the sample was mixed with an equal volume of a reaction mixture to provide a final concentration of 50 mM Tris (pH 8.5), 6 mM MgCl$_2$, 10 mM dithiothreitol (DTT), 2.0 µg bovine serum albumin (BSA), 0.5 µCi TTP, 80 mM KCl, and 0.05% Triton X-100. The reaction was initiated by the addition of 1.0 µl of HIV reverse transcriptase (containing~1 ng protein; from American BioTechnology, Cambridge, Mass.; Cat. No. 26001). After 1 hour incubation at 37° C., the reaction was stopped by the addition of 5.0 µof stop buffer (50 mM EDTA+3% SDS). The reverse transcriptase products (polymerization products) were separated from the unincorporated label by chromatography on Sephadex G-25 (superfine) columns. The fractions corresponding to the void volume were collected and counted by scintillation counting. The inhibition of HIV reverse transcriptase by zidovudine triphosphate was determined using known amounts of zidovudine triphosphate, both in buffer and in the presence of cell extracts from normal peripheral blood mononuclear cells, to obtain standard curves which were used to estimate the amount of zidovudine triphosphate in assay samples.

Results

Standard curve. FIG. 1 shows typical inhibition kinetics by zidovudine triphosphate of HIV reverse transcriptase catalyzed incorporation of TTP into product using poly[rA] -oligo[dT]$_{12-18}$ as template-primer. These results (expressed as the reciprocal of the incorporation of radioactivity) show linear inhibition kinetics (coefficient of regression of 0.99) over a concentration of zidovudine triphosphate ranging from 10 to 500 fmol. The invention overcomes a potential problem with using an enzymatic assay for measuring zidovudine triphosphate in biological material, which is the dilution of [$^3$H]TTP by endogenous deoxynucleotides, particularly TTP. FIG. 1 shows the effect of spiking the standard curve with extract of peripheral blood mononuclear cells from about 10$^6$ cells (which was the amount routinely assayed in patient samples). There is some decrease of the radioactivity incorporated from [$^3$H]TTP (as indicated by an increase in the y-intercept) but the standard curve still gave good linear kinetics over the concentration of zidovudine triphosphate being evaluated (R>0.98). Other metabolites including zidovudine-MP, and thymidine monophosphate (TMP) were also tested for inhibition of reverse transcriptase activity but they did not affect the reaction kinetics at concentrations of up to 10,000 fmols.

Example 2

HPLC Determination of Zidovudine Triphosphate Levels in CEM Cell Extracts

To determine whether it was possible to quantitate the level of zidovudine triphosphate in extracts from cells exposed to zidovudine with the reverse transcriptase assay (see Example 1), HPLC analysis was compared with the reverse transcriptase assay.

T-lymphoid CEM cells were incubated with 1 µM [3H] zidovudine for 4 hours and split into 3 fractions. One fraction was analyzed by HPLC and zidovudine metabolites were quantitated by usual radioisotopic methods. The other two cell fractions were used to quantitate zidovudine triphosphate by the RIA (see Example 3) and reverse transcriptase assays (see Example 1).

HPLC separation of zidovudine metabolites. Radioactive cell extracts were analyzed for zidovudine metabolite concentration by separating the radioactive zidovudine metabolites on a 250 mm Whatman partisil-10 SAX anion exchange column and collecting the fractions for scintillation counting. Buffers used in the separation procedure were A—0.005M ammonium phosphate at pH 4.0+10% methanol and B—0.7M ammonium phosphate at pH 4.6+10% methanol. The gradient used for the separation of zidovudine metabolites was 20 min at 0%, B, a 16 min concave gradient from 0–100% B and finally 8 min at 100% B. A flow rate of 1.5 ml/min was used and fractions were collected every 40 seconds and analyzed by liquid scintillation counting.

Results

As shown in Table 1, results of zidovudine triphosphate levels in CEM cells after incubation with 1 µM zidovudine from the HPLC method was in good agreement with the reverse transcriptase and RIA methods.

TABLE 1

Comparison of Zidovudine Triphosphate Levels in CEM Cells by Various Analytical Methods

| Method of Determination | Zidovudine Triphosphate (pmol/10$^6$ cells) | n |
|---|---|---|
| HPLC-Radioactive | 1.42 | 1 |
| HPLC-RIA | 1.50 ± 0.65 | 3 |
| Reverse Transcriptase Bioassay | 1.39 ± 0.17 | 3 |

Intracellular zidovudine triphosphate concentrations were determined in CEM cells after a 4 hr incubation with 1 µM zidovudine in the presence of 1 µCi/ml of [$^3$H]-zidovudine. Cell extracts were analyzed and quantified by using the different assays as described in Materials and Methods. Statistical parameters represent the standard deviation of the mean (δ) of three determinations of parallel samples.

Based on a close correlation between cellular levels of zidovudine triphosphate obtained by the bioassay and by HPLC radioisotopic assay, the precision and specificity of the bioassay will provide accurate quantitation of zidovudine triphosphate levels in extracts of peripheral blood mononuclear cells from patients treated with therapeutic doses of zidovudine (see Example 6).

Example 3

HPLC-RIA Determination of Zidovudine Triphosphate From CEM Cells

To further compare the reverse transcriptase assay method with other standard methods for quantitating zidovudine levels, HPLC-RIA techniques (Kuster et al., *J. Infect. Dis.* 164:773–776 (1991)) were utilized.

CEM cells were extracted in the same manner as cultured peripheral blood mononuclear cell samples (see Materials and Methods). The zidovudine metabolites were separated by anion exchange HPLC using essentially the same buffers as described previously but using a gradient of 10 min at 0% B, a 26 min concave gradient and 10 min at 100% B to further separate the di- and triphosphates from the zidovudine monophosphate. The fractions containing zidovudine triphosphate were pooled, vacuum desiccated to ~2 ml and treated with acid phosphatase at 37 ° C. overnight to remove the phosphate groups. The samples were cleaned up using Waters Sep-pak C-18 cartridges. The cartridges were conditioned with 10% methanol and then rinsed with water. Each sample was applied separately and eluted with 50% methanol. The samples were vacuum desiccated to a volume under 500 μl and further purified with a 250 mm Whatman ODS-3 column. Buffer A was 35% methanol and buffer B was 50% methanol. The gradient was 15 min at 0% B followed by 20 min at 100% B with a flow rate of 0.5 ml/min and fractions collected every min. The fractions containing zidovudine were pooled and vacuum desiccated to dryness. The samples were resuspended in sample dilution solution provided in the kit and analyzed for zidovudine as described with modifications as described elsewhere (Slusher et al., *Agents Chemother.* 36:2473–2477 (1992)). The antibody was diluted 1:3 and preincubated with the sample 2 hours. A 1:6 dilution of the [$^{125}$I]zidovudine was added and incubated at room temperature for another 2 hours and finally the volume of antibody precipitating complex was reduced to 300 μl.

Results

As shown in Table 1 (See Example 2) results of zidovudine triphosphate levels in CEM cells after incubation with 1 μM zidovudine from the HPLC-RIA method was in good agreement with the reverse transcriptase and HPLC methods.

Similar to the close correlation between cellular levels of zidovudine triphosphate obtained by the bioassay and by HPLC radioisotopic assay, there is also a close correlation between cellular levels of zidovudine triphosphate obtained by the bioassay and by an RIA technique. Again these data demonstrate that the precision and specificity of the bioassay seem will provide accurate quantitation of zidovudine triphosphate levels in patients.

Example 4

Zidovudine Triphosphate Levels in Peripheral Blood Mononuclear Cells In Vitro

In order to assess the usefulness of the reverse transcriptase assay in measuring intracellular concentrations in peripheral blood mononuclear cells, zidovudine triphosphate levels were determined in quiescent or PHA-stimulated peripheral blood mononuclear cells incubated with 1 μM [$^3$H]zidovudine.

Results

Figure 2A:
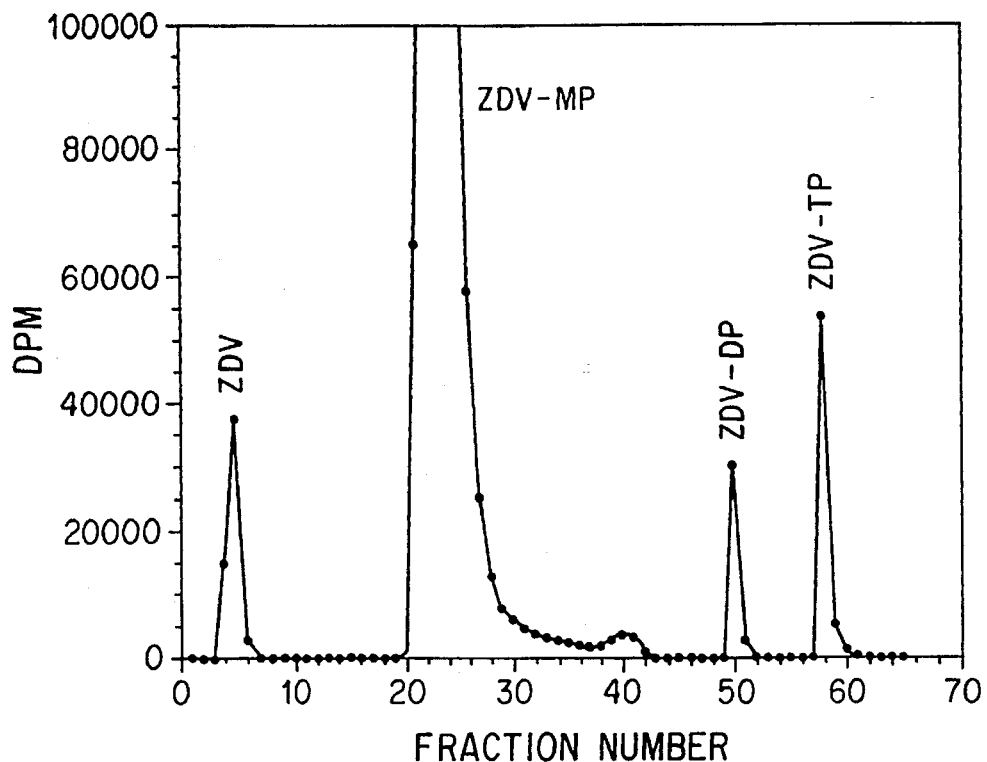
FIGS. 2A and 2B depict HPLC separation of zidovudine metabolites in PHA-P stimulated and resting peripheral blood mononuclear cells. Zidovudine metabolites from stimulated (A) or resting (B) peripheral blood mononuclear cells incubated with 1 µM [$^3$H]-zidovudine were separated by anion exchange HPLC and metabolite concentrations determined by scintillation counting of the radioactive fractions.
Figure 2B:
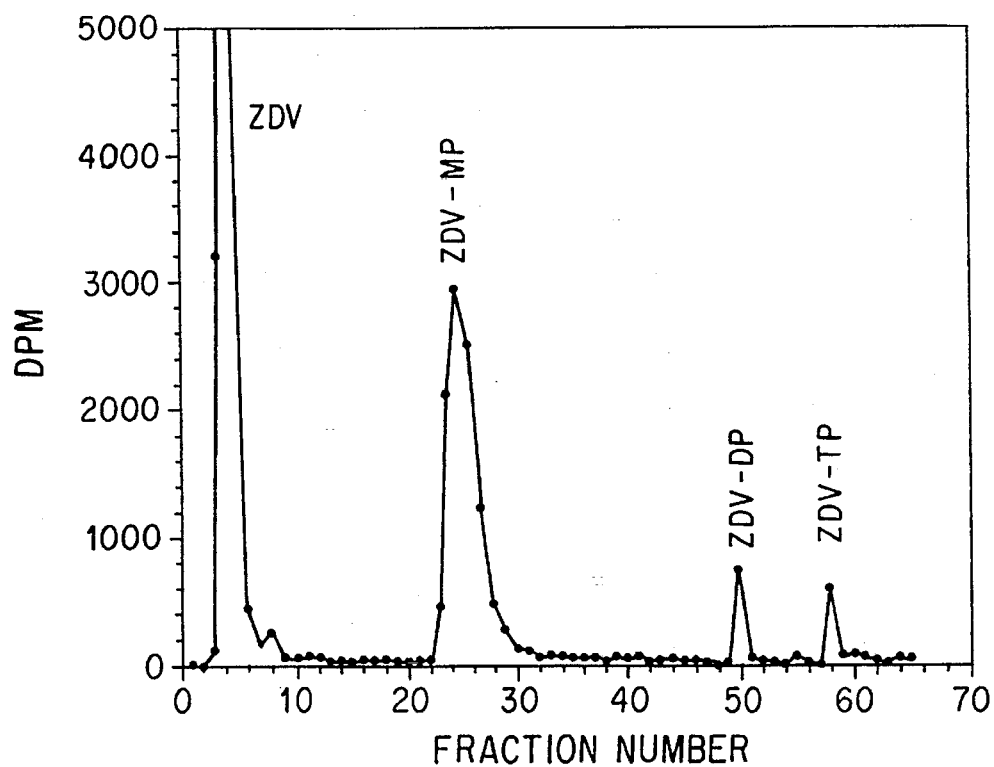

Proliferating peripheral blood mononuclear cells had a high phosphorylation rate of zidovudine when compared to resting peripheral blood mononuclear cells (FIG. 2). To determine the stability of zidovudine during isolation of peripheral blood mononuclear cells by Ficoll-Hypaque PHA-stimulated cells were incubated with 1 μM [$^3$H]zidovudine for 4 hours and divided into two fractions. One fraction was extracted with 70% methanol and the second was layered on Ficoll-Hypaque and purified as whole blood.

Recovery of [$^3$H]zidovudine metabolites after the separation procedure were greater than 90% indicating that zidovudine metabolites are stable during Ficoll-Hypaque isolation.

Example 5

Correlation of Reverse Transcriptase Bioassay for Detection of Zidovudine Triphosphate With the Radioisotopic Method PHA-stimulated peripheral blood mononuclear cells were incubated with a range of labeled zidovudine concentrations for 4 hours and samples of these extracts diluted to provide a wide range of concentrations. These samples were divided into two fractions and one fraction was analyzed by the HPLC-radioisotopic method and the other by the reverse transcriptase assay. A zidovudine-free extract served as the control to eliminate cell background for the bioassay.

Results

FIG. 3 shows a scatter plot of radioisotopic measurements versus concurrent measurement of zidovudine triphosphate by the reverse transcriptase assay. The data distribution around the line of unity indicated good agreement between the two methods with a slight bias towards higher estimates with larger concentrations of zidovudine triphosphate.

Example 6

Intracellular Zidovudine Triphosphate and Plasma Zidovudine Levels in HIV-Infected Volunteers Zidovudine Triphosphate in peripheral blood mononuclear cells and plasma zidovudine concentrations were measured in 12 HIV-infected adult volunteers receiving zidovudine at St. Jude Children's Research Hospital. All 12 volunteers studied were administered a single 100 or 500 mg oral dose of zidovudine. Plasma zidovudine concentrations and intracellular zidovudine triphosphate levels were determined at 1, 2, 4, and 6 hours after administration of the drug. The zidovudine-free peripheral blood mononuclear cells from each individual at baseline (untreated) served as the cell background to construct the standard curve for zidovudine triphosphate determination. Zidovudine Triphosphate could be measured in all 12 volunteers after zidovudine administration.

Zidovudine was determined in the plasma of HIV-infected volunteers by RIA to ascertain the relationship between zidovudine concentrations and intracellular zidovudine triphosphate.

Pharmacokinetic studies in patients. To assess the utility and sensitivity of the bioassay of the invention in patients, a clinical study was performed. The study was approved by the Institutional Review Board of St. Jude Children's Research Hospital and informed consent was obtained from each individual according to institutional procedures.

Individuals in this study were HIV-infected individuals recruited from an area clinic. All patients had received no prior zidovudine therapy and were in good health. After informed consent, a single dose of zidovudine, 100 or 500 mg, was administered orally. Samples of peripheral blood (20 mL) were obtained at baseline (untreated) and at 1, 2, 4, and 6 hours after the dose of zidovudine. CD4 and CD8 cell counts were determined from baseline samples. Plasma zidovudine concentrations were determined by RIA and intracellular zidovudine triphosphate was determined after zidovudine administration.

Pharmacokinetic parameters for a one compartment model (oral clearance, $CL_o$; half-life, $t_{1/2}$; apparent volume of distribution, $V_{app}$; and absorption rate, $K_a$) were estimated from plasma zidovudine concentrations for each individual using Bayesian estimation as implemented in the ADAPTII modeling software (Biomedical Simulation Resource, University of Southern California, Los Angeles, Calif. 90089). Prior distributions for the parameters were assumed to be log normally distributed with known but independent variances (i.e., no parameter covariance) and were taken from previous studies in similar patients (Flether et al., *Pharmacotherapy* 12:429–434 (1992)). For absorption, both zero and first order inputs were examined and similar results were obtained for the remaining parameters ($CL_o$, $V_{app}$) with no difference in the criterion value for convergence. First order absorption was selected as most consistent with previous pharmacokinetic reports.

Radioimmunoassay for plasma zidovudine. Plasma samples were heat inactivated at 56° C. for 4 hours prior to assay. The samples were diluted to obtain values within a standard curve range of 10–200 ng/ml with 200 µl of sample. One hundred µl of [$^{125}$I]-zidovudine and 100 µl of antibody directed against zidovudine were added to the 200 µl sample, vortexed, and incubated at room temperature for 2 hours. Five-hundred µl of a secondary antibody precipitating complex was added and incubated for 20 min at room temperature. The resultant mixtures were centrifuged, the supernate decanted, and the precipitate counted using an LKB gamma counter connected to an IBM PC computer with an RIA Calif. LC software program.

Results

Figure 4:
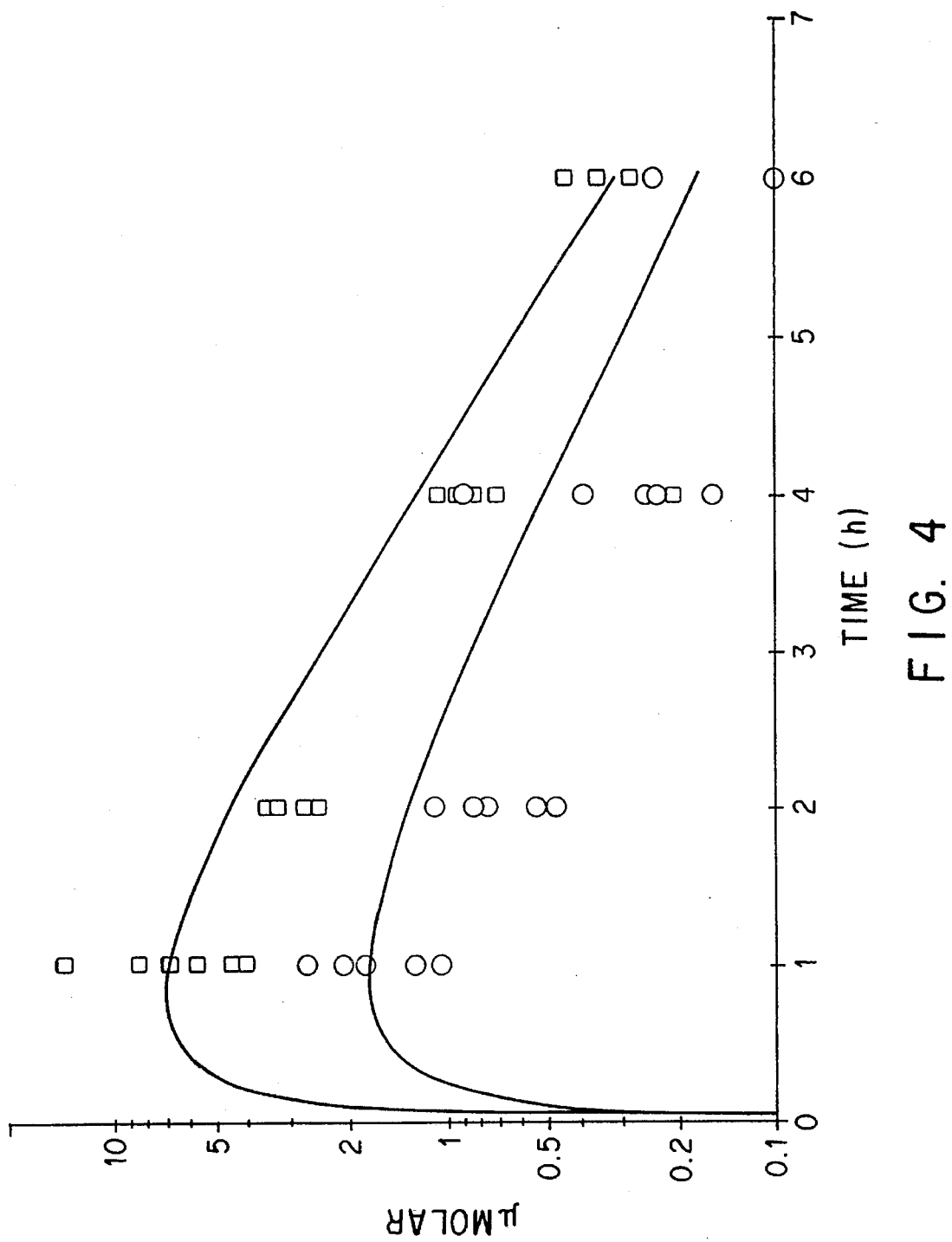
FIG. 4 depicts plasma zidovudine concentrations in HIV-Infected individuals. Volunteers were administered a single 100 mg (○) or 500 mg (□) dose of zidovudine. Symbols are data for each subject and the solid line is a simulation for media parameters determined for each of the two dose levels.

Table 2 (below) shows that median plasma zidovudine concentrations at 1 hour were 1.79 M/1 for the 100 mg dose and 6.3 µmol/1 for the 500 mg dose. There was substantial variability in plasma zidovudine concentrations at any single time point, even for patients receiving the same dose, with coefficients of variation (% CV) ranging from 18% to 77%. FIG. 4 shows the plasma zidovudine concentrations from volunteers given 100 or 500 mg of zidovudine and the predicted concentrations from the median parameters estimated for each group. Median $CL_o$ (1.28 l/h/kg) in the 100 mg group of individuals were approximately 80% the median $CL_o$ (1.56 l/h/kg) for the individuals given 500 mg but the two groups were not significantly different (p>0.2 by the Mann-Whitney U test). This substantially lower $CL_o$ in the low dose group resulted in systemic exposures between the two groups, as reflected by AUC, the differed by a ratio of approximately 4 rather than 5 as would be predicted only from the dose ratio.

TABLE 2

Summary of Plasma Zidovudine Concentration in Patients Administered 500 or 100 mg of Zidovudine

| Time (h) | 100 mg Zidovudine Dosage | | | 500 mg Zidovudine Dosage | | |
|---|---|---|---|---|---|---|
| | Median | Range | % CV* | Median | Range | % CV* |
| | (µM Plasma Zidovudine) | | | | | |
| 1 | 1.79 | 1.07–2.7 | 37 | 6.3 | 5.7–14.0 | 50 |
| 2 | 0.76 | 0.48–1.1 | 34 | 3.0 | 0.8–3.54 | 38 |
| 4 | 0.26 | 0.16–0.9 | 77 | 0.9 | 0.21–1.09 | 39 |
| 6 | ND# | | | 0.36 | 0.36–0.45 | 18 |
| $t_{1/2}$ | 1.29 | 0.8–1.6 | 26 | 1.07 | 0.7–1.2 | 21 |
| $CL_0$ | 1.28 | 0.86–2.1 | 36 | 1.56 | 1.2–2.75 | 35 |
| AUC | 1.2 | 0.8–1.8 | 31 | 4.2 | 2.1–6.2 | 33 |

*% CV = (standard deviation/mean) × 100. Results are from five patients administered 100 mg zidovudine and six patients administered 500 mg zidovudine followed for the indicated time period. $t_{1/2}$ = half life (h). $CL_0$ = oral clearance (l/h/kg). AUC = area under the curve (mg/l*h). #ND, plasma zidovudine concentration below standard curve in 4 of 5 patients.

Intracellular zidovudine triphosphate levels ranged from 3 to 326 fmol/10$^6$ cells with a % CV range of 52–157% indicating a higher variation in zidovudine triphosphate levels than in plasma zidovudine concentrations (Table 3 (below)). In parallel incubations, the extracts of zidovudine treated patients were spiked with a known concentration of zidovudine triphosphate as shown in Table 4 (below). The measured concentrations of spiked samples by the reverse transcriptase assay had an average variation of about 20% from the expected zidovudine triphosphate levels. Zidovudine triphosphate values increased from 1 to 2 hours (Table 3 (below)) and then remained at a plateau value through 6 hours that was consistent within patients but quite variable between individuals. The median plateau value (average of the 2, 4, and 6 hours measurements) at the 500 mg dose was 68 and 41 for the 100 mg dose. This proportion of 1.7 is in contrast to the systemic AUC ratio of 4 noted above.

TABLE 3

Zidovudine Triphosphate Concentration in Peripheral Blood Mononuclear Cells of Patients Administered 100 or 500 mg Zidovudine

| Time (h) | 100 mg Zidovudine Dosage | | | 500 mg Zidovudine Dosage | | | Median Ratio (500/100) |
|---|---|---|---|---|---|---|---|
| | Median | Range | % CV* | Median | Range | % CV* | |
| | Zidovudine Triphosphate (fmol/10$^6$ cells) | | | | | | |
| 1 | 5 | 1–49 | 157 | 42 | 28–98 | 52 | 8.4 |
| 2 | 57 | 11–207 | 95 | 92 | 1–182 | 80 | 1.6 |
| 4 | 52 | 11–89 | 62 | 63 | 19–76 | 35 | 1.5 |
| 6 | 37 | 24–326 | 118 | 78 | 1–207 | 79 | 2.1 |

*% CV = (standard deviation/mean) × 100. Results were from six patients administered the indicated dose of zidovudine.

TABLE 4

Variations from Expected Concentrations of Samples Spiked with Zidovudine Triphosphate

| Time (h) | 100 mg Dosage | | 500 mg Dosage | |
|---|---|---|---|---|
| | Mean | Range | Mean | Range |
| | percent | | | |
| 1 | 33.3 | 12.8–58.3 | 16.6 | 11.1–21.0 |
| 2 | 15.2 | 0.5–36.3 | 17.5 | 7.6–28.0 |
| 3 | 21.6 | 2.5–33.6 | 14.2 | 3.2–28.6 |
| 4 | 11.1 | 3.0–19.9 | 21.7 | 9.4–30.3 |

Aliquots of patient extract were spiked with 0.1 pmol of zidovudine triphosphate and the concentration determined with the enzymatic assay. The data are the means from 5 patients administered 100 mg of zidovudine or 4 patients administered 500 mg of zidovudine.

Conclusions

The potential drawback associated with a bioassay using cell extracts is the inability to differentiate zidovudine triphosphate from interfering endogenous nucleotides. However, this potential problem has been overcome in the invention by including in each determination the patient's own zidovudine-free PBL extract to construct the standard curve.

In addition, the accuracy of zidovudine triphosphate levels were determined by obtaining the result of the reverse transcriptase assay spiked with a known concentration of zidovudine triphosphate. The average variation from expected values (20%) was less than sample variation (30%) seen with RIA measurement by Slusher et al. (Slusher et al., *Agents Chemother.* 36: 2473–2477 (1992)).

These data describing systemic and cellular pharmacokinetics of zidovudine suggest a relationship between systemic exposure and cellular metabolism to the active form. Increased doses yielded increased plasma AUC and increased zidovudine triphosphate in cells.

Our results with the reverse transcriptase bioassay of the patient samples are similar to those reported by Slusher et al. (Slusher et al., *Antimicrob. Agents Chemother.* 36:2473–2477 (1992)). These workers using HPLC-RIA assay reported levels of 50–140 fmol/$10^6$ cells of zidovudine triphosphate in peripheral blood mononuclear cell extracts of seven patients 2 hr after receiving a 300 mg dose of oral zidovudine. We observed average peak zidovudine triphosphate levels of 107 and 119 fmol/$10^6$ cells, after 100 and 500 mg doses, respectively.

By contrast, our results were markedly different from those of Toyoshima et al. (Toyoshima et al., *Anal. Biochem.* 196:302–307 (1991)) who reported 10-fold higher levels of zidovudine triphosphate in peripheral blood mononuclear cells from AIDS patients receiving a 300 mg oral dose zidovudine using an elaborate and cumbersome HPLC column switching and UV spectrophotometric method.

Relatively small numbers of zidovudine treated peripheral blood mononuclear cells were needed for this bioassay (10–15×$10^6$ cells), a number which could be obtained from 10–20 ml of blood.

Several important observations resulted from the present measurements. First, we were able to measure zidovudine triphosphate in blood samples from patients receiving zidovudine without the use of radiolabeled drug and the elaborate separation by HPLC required by RIA. With simple modification, this assay will be adaptable to analysis of other thymidine analogs such as stavudine and other dideoxynucleotide analogs in clinical use. Second, a relationship between the systemic pharmacokinetics of zidovudine and intracellular zidovudine triphosphate is indicated by the increase in the median zidovudine triphosphate values as dose and systemic AUC are increased. However, the time frame for these measurements will have to be extended to allow a quantitative assessment of the importance of systemic exposure (e.g., plasma AUC) to intracellular zidovudine triphosphate formation. Third, there appears to be a larger variation in intracellular zidovudine triphosphate than in the plasma zidovudine concentrations. The greater variability may be caused by differences in metabolism introduced by phosphorylation of zidovudine. This supports the notion of continued measurement of zidovudine triphosphate levels directly and raises questions as to the actual time frame of intracellular zidovudine triphosphate degradation. Thus, the enzymatic assay will be of significant value in the more extensive studies of the intracellular pharmacology of zidovudine and other such antiviral compounds required to correlate such observations with therapeutic activity and toxicity.

Incorporation by Reference

All publications cited herein are incorporated fully into this disclosure by reference.

From the foregoing it will be appreciated that, although specific embodiments of the invention have been described herein for purposes of illustration, various modifications may be made without deviating from the spirit and scope of the invention and the following claims. As examples, the steps of the preferred embodiment constitute only one form of carrying out the process in which the invention may be embodied.

What is claimed is:

1. A method for determining intracellular levels of a nucleoside reverse transcriptase inhibitor or metabolites thereof in an individual treated with said nucleoside reverse transcriptase inhibitor or metabolites thereof, said method comprising:

a. obtaining a bodily sample suspected to contain said nucleoside reverse transcriptase inhibitor or metabolites thereof;

b. detecting the inhibitor or metabolites thereof in the sample using a reverse transcriptase assay.

2. The method of claim 1 wherein said inhibitor is a metabolite of zidovudine.

3. The method of claim 2 wherein said metabolite is zidovudine triphosphate.

4. The method of claim 1 wherein said assay comprises obtaining a cell from said individual.

5. The method of claim 4 wherein said cell is a peripheral blood mononuclear cell.

6. The method of claim 1 wherein said detecting step further comprises the steps of:

(a) detecting a lowered level of RNA-dependent DNA polymerization by said reverse transcriptase in a treated individual;

(b) comparing said level of step (a) with a level of RNA-dependent DNA polymerization detected in a bodily sample from an untreated individual or said treated individual prior to treatment; and (c) determining the amount of reverse transcriptase inhibitor by relating results obtained from the comparison of step (b) with step (a) to a standard curve.

7. The method of claim 1 wherein said detecting step (b) further comprises contacting reverse transcriptase with a template and primer.

8. The method of claim 1 wherein said sample is from an individual having a disease selected from the group consisting of:

HIV 1 or HIV 2 infection, AIDS, Kaposi's sarcoma, pneumocytis pneumonia, mycobacterium infection, AIDS Related Complex, AIDS dementia or systemic candidiasis.

9. A method for determining intracellular levels of a nucleoside reverse transcriptase inhibitor or a metabolite thereof in an individual being treated with a therapeutic compound or metabolite thereof used to treat a retrovirus infection, said method comprising:

a. obtaining a bodily sample suspected to contain a reverse transcriptase inhibitor;

b. detecting the inhibitor in the sample using a reverse transcriptase assay.

10. The method of claim 9 wherein said metabolite is a metabolite of zidovudine.

11. The method of claim 10 wherein said metabolite is zidovudine triphosphate.

12. The method of claim 9 wherein said assay comprises obtaining a cell from said individual.

13. The method of claim 12 wherein said cell is a peripheral blood mononuclear cell.

14. The method of claim 9 wherein said determining step further comprises the steps of:

(a) detecting a lowered level of RNA-dependent DNA polymerization by said reverse transcriptase;

(b) comparing said level of step (a) with a level of RNA-dependent DNA polymerization detected in a bodily sample from an untreated individual or said treated individual prior to treatment; and (c) determining the amount of reverse transcriptase inhibitor by relating results obtained from the comparison of step (b) with step (a) to a standard curve.

15. The method of claim 9 wherein said determining step further comprises contacting substantially purified reverse transcriptase with a template and primer.

16. The method of any of claims 1 or 9 wherein the reverse transcriptase in said reverse transcriptase assay is derived from a virus selected from the group consisting of:

Cisternavirus A, Oncovirus B, Oncovirus C, Oncovirus D, Hepadnavirus, Caulimoviruses, simian immunodeficiency viruses, feline immunodeficiency viruses, equine infectious anemia virus, human T cell leukemia virus, and human immunodeficiency virus.

17. The method of claim 1 or 9 wherein said nucleoside reverse transcriptase inhibitor, said therapeutic compound or a metabolite of either is selected from the group consisting of: zidovudine, dideoxynucleotide triphosphate analogs, 2',3'-dideoxynucleoside 5'-triphosphates; dideoxyinosine and dideoxycytidine; anti-reverse transcriptase antibodies, anti-reverse transcriptase sFvs; Carbovir, a carbocyclic analog of 2',3'-didehydro-2',3'-dideoxyguanosine; 3'-azido-3'-deoxythymidine 5'-($\alpha,\beta$-imido)-triphosphate; 3'-azido-3'-dideoxythymidine 5'-($\alpha,\beta$-imido)-triphosphate; 3'-azido-3'-deoxythymidine 5'-($\alpha,\beta$-imido)-triphosphate; dideoxythymidine 5'-($\alpha,\beta$-imido)-triphosphate; 3'-azidothymidine 5'-($\beta,\gamma$-imido)-triphosphate; 5'-($\alpha,\beta:\beta,\gamma$-diimido)-triphosphate, 3'-deoxy-2',3'-didehydrothymidine 5'-triphosphate; R82913, (+)-S-4, 5, 6, 7-tetrahydro-9-2 chloro-5-methyl-6-(3-methyl-2-butenyl)-imidazo(4,5,1-jk)-(1,4)-benzodiazepin-(1H)-thione, a TIBO derivative; 2',3'-didehydro-2',3'-didehydro-2',3'-dideoxythymidine triphosphate; 5'-triphosphates of 3'-azido-3'-deoxythymidine, 2',3'-dideoxynucleosides; 5'-triphosphates of carbovir, 3'-deoxythimidine, threo- and erythro- isomers of 3'-azido-3'-deoxythimidine triphosphate; 2',3'-didehydro-2',3'-dideoxythimidine, D4T; purines comprising a 2', 3'-dideoxyribose moiety; nucleosides comprising a 2',3'-didehydro-2',3'-deoxyribose moiety; 2',3'-dideoxythymidinene, ddE Thd; 3-{((4,7-dichloro-1,3-benzoxazol-2-yl)methyl)amino}-5-ethyl-6-methylpyridin-2(1H)-one; 3'-azido-2',3'-dideoxyadenosine, AZA; 3'-azido-2'-3'-dideoxyguanosine, AZG, carbovir triphosphate, the 5'-triphosphates of carbovir; carbovir monophosphate; (-Et, -nPr, -nPre, -iPre, -Ce)5'-triphosphates of 5'-substituted 2'-deoxy-uridine; phosphonoacidic acid; phosphonoformic acid; zidovudine monophosphate; zidovudine diphosphate; 2',3'-dideoxynucleosides; Ribavirin; AZT plus interferon; anhydro-AZT; and anhydro-N3, -UdR.

* * * * *